US010330462B2

United States Patent
Arieli et al.

(10) Patent No.: US 10,330,462 B2
(45) Date of Patent: Jun. 25, 2019

(54) SYSTEM FOR ANALYZING OPTICAL PROPERTIES OF AN OBJECT

(71) Applicant: ADOM, ADVANCED OPTICAL TECHNOLOGIES LTD., Lod (IL)

(72) Inventors: Yoel Arieli, Jerusalem (IL); Yoel Cohen, Nes Ziona (IL)

(73) Assignee: ADOM, Advanced Optical Technologies Ltd., Lod (IL)

( * ) Notice: Subject to any disclaimer, the term of this patent is extended or adjusted under 35 U.S.C. 154(b) by 0 days.

(21) Appl. No.: 16/013,664

(22) Filed: Jun. 20, 2018

(65) Prior Publication Data
US 2018/0299252 A1 Oct. 18, 2018

Related U.S. Application Data

(63) Continuation of application No. 15/502,147, filed as application No. PCT/IL2015/050808 on Aug. 7, 2015, now Pat. No. 10,024,650.

(60) Provisional application No. 62/036,132, filed on Aug. 12, 2014.

(51) Int. Cl.
| | |
|---|---|
| *G01J 3/02* | (2006.01) |
| *G01B 9/02* | (2006.01) |
| *G01J 3/447* | (2006.01) |
| *G01J 3/453* | (2006.01) |
| *G01N 21/31* | (2006.01) |

(52) U.S. Cl.
CPC ..... *G01B 9/02091* (2013.01); *G01B 9/02019* (2013.01); *G01J 3/0208* (2013.01); *G01J 3/0224* (2013.01); *G01J 3/447* (2013.01); *G01J 3/453* (2013.01); *G01N 21/31* (2013.01); *G01N 2201/0636* (2013.01); *G01N 2201/0683* (2013.01)

(58) Field of Classification Search
CPC . G01B 9/02091; G01J 3/00; G01J 3/02; G01J 3/0224; G01J 3/45
See application file for complete search history.

(56) References Cited

U.S. PATENT DOCUMENTS

| | | | | |
|---|---|---|---|---|
| 4,548,502 A * | 10/1985 | Chandra | ................. | G01B 9/02 356/510 |
| 4,768,182 A * | 8/1988 | Hatfield | ................. | G01B 11/06 356/497 |
| 7,038,782 B2 * | 5/2006 | Hedin | ................. | G01J 9/0246 356/454 |

(Continued)

*Primary Examiner* — Jonathan M Hansen
(74) *Attorney, Agent, or Firm* — Workman Nydegger

(57) ABSTRACT

Apparatus and methods are described including a line spectrometer that receives a point of light. The line spectrometer includes a first optical element, and a second optical element configured to convert the point of light to a line of light and to direct the line of light toward the first optical element. The first optical element defines first and second surfaces, a distance between the first and second surface varying as a function of distance along the first optical element, the first optical element thereby being configured to generate first and second reflected lines of light that reflect respectively from the first and second surfaces. A detector array receives the first and second lines of light, and generates an interferogram in response thereto. A computer processor determines a spectrum of the point of light, by analyzing the interferogram. Other applications are also described.

22 Claims, 3 Drawing Sheets

(56) References Cited

U.S. PATENT DOCUMENTS

2010/0328659 A1* 12/2010 Bodkin .................... G01J 3/02
                                                356/326
2013/0222801 A1*  8/2013 Harel ........................ G01J 3/10
                                                356/328

* cited by examiner

SYSTEM FOR ANALYZING OPTICAL PROPERTIES OF AN OBJECT

CROSS-REFERENCE TO RELATED APPLICATIONS

This application is a continuation of U.S. Ser. No. 15/502,147 to Arieli (published as US 2017/0241766), which is the US national phase of International Application PCT/IL2015/050808 to Arieli (published as WO 16/024270), filed Aug. 7, 2015, which claims priority from U.S. Provisional Application 62/036,132 to Arieli, filed Aug. 12, 2014.

FIELD OF THE INVENTION

The present invention relates to tomography measurements, and more particularly, to a system for measuring the surface and layers thicknesses of an object.

BACKGROUND OF THE INVENTION

Commercially available Optical Coherence Tomography (OCT) systems are employed in diverse applications, including diagnostic medicine such as ophthalmology, where they are used to obtain images of the retina.

In conventional interferometry with long coherence length (laser interferometry), interference of light occurs over long distances. In white light OCT, which is based on broadband light sources, the interference is shortened to a distance of micrometers owing to the short coherence lengths of the light sources (the coherence length is reciprocal to the bandwidth of the light source).

In dual path interferometry, the incoming light is split into two arms—a sample arm (containing the item of interest) and a reference arm (usually a mirror). The combination of the reflected light from the object in the sample arm and reference light reflected from the mirror in the reference arm gives rise to an interference pattern. In interferometry with short coherence length such as OCT, interference patterns are obtained only when the optical path difference (OPD) between the light from both arms is less than the coherence length of the light source.

Time Domain OCT (TD-OCT)

In time domain OCT, the mirror in the reference arm is progressed longitudinally in time. Since the fringes are obtained only when the OPD is shorter than the coherence length of the light source, the envelope of the visible fringes changes as the OPD varies, the peak of the envelope corresponding to zero OPD. This interference is called auto-correlation and the intensity of the interference as a function of the OPD is called an interferogram. By scanning the mirror in the reference arm and measuring the OPD where the peak of the envelope is obtained, the height profile of the sample can be obtained.

Frequency Domain OCT (FD-OCT)

In frequency domain OCT, the mirror in the reference arm is fixed and the broadband interference is acquired by measuring the spectrum of the reflected light. According to the Wiener-Khintchine theorem there is a Fourier relation between the interferogram and the spectral power density. The interferogram and thus the depth scan can be calculated by Fourier-transforming the measured spectrum of the reflected light. The FD-OCT improves the imaging speed, reduces losses during the scan and improves the signal to noise ratio compares to TD-OCT.

Swept Source OCT (SW-OCT)

In SW-OCT, the mirror in the reference arm is fixed but the spectral components are encoded in time. The spectrum is either filtered or generated in a series of successive frequency steps. The measured reflected light as a function of optical frequency is Fourier-transformed to obtain the interferogram.

Scanning

The systems described above are based on single point depth information obtained by the OCT; hence they scan the sample in two lateral dimensions and reconstruct a three-dimensional image of the object. The cross-sectional scan is called B-scan.

The FD-OCT and the SW-OCT have much higher signal to noise ratio (SNR) than the TD-OCT, but need expensive optical devices such as a high resolution spectrometer and a tunable laser.

Therefore there is a need for a new method for low-cost OCT which still has high SNR.

SUMMARY OF THE INVENTION

In accordance with the present invention there is provided a system for analyzing and measuring optical properties of an object by using Spatial Domain Optical Coherence Tomography (SD-OCT) where the spectrograms are obtained by means of spatial domain interferometry.

In one embodiment the SD-OCT is obtained by a dual path interferometer where a line on the object is illuminated by a point light source by means of an optical system employing cylindrical lenses.

In accordance with some embodiments the spectrum of light is measured by means of Fourier transform spectroscopy based on birefringence.

In accordance with some embodiments the spectrum of light is measured by means of Fourier transform spectroscopy based on a line spectrometer that creates "Equal Inclination fringes" interferometry.

In accordance with some embodiments the spectrum of light is measured by means of Fourier transform spectroscopy based on a line spectrometer that creates "Equal Thickness fringes" interferometry.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 2b shows an interferogram being the intensity function of a line of light seen by the spectrometer in FIG. 2a;

FIG. 3b shows an interferogram being the intensity function of a line of light seen by the spectrometer in FIG. 3a;

FIG. 4b shows an interferogram being the intensity function of a line of light produced by the wedge in FIG. 4a;

DETAILED DESCRIPTION OF EMBODIMENTS

In the following description of some embodiments, identical components that appear in more than one figure or that share similar functionality will be referenced by identical reference symbols.

Figure 1:
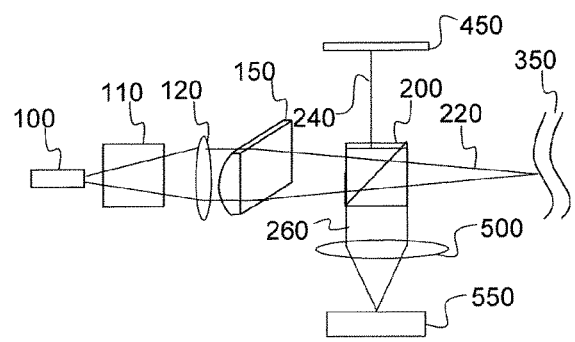
FIG. 1 shows schematically full field 2D OCT based on a dual path interferometer.

FIG. 1 shows schematically a full field 2D OCT according to a first embodiment. The system consists of a point light source 100, an optional spectral modulator 110, a collimator 120, an optional cylindrical lens 150, a beam splitter 200, a layered object 350, a reference mirror 450, an imaging system 500 and an analyzer 550, which may be realized in practice by an imaging spectrometer also known as a hyperspectral camera. In some cases the imaging spectrometer or hyperspectral camera is replaced by an array of detectors. For the sake of clarity, the following description will refer generally to "analyzer 550" and specific implementations will be mentioned without enumeration.

Light emanating from the point light source 100 is expanded and collimated by the collimator 120, divided by the beam splitter 200 into two beams: a probing beam 220 (constituting a first portion) and a reference beam 240 (constituting a second portion). The probing beam 220 is directed as an illuminated line toward the object and the reference beam 240 is directed as an illuminated line toward a reference mirror 450. The line of the object thus illuminated will be referred to as an "object line". The light beams 220 and 240 returning from the object 350 and the reference mirror 450 as illuminated lines are recombined collinearly by the beam splitter 200 to form a combined beam 260 that is directed by the imaging system 500 as an image line on to an analyzer 550. The imaging system 500 also images the object 350 on the analyzer 550. The analyzer is typically constituted by an imaging spectrometer also referred to as a hyperspectral camera or on an array of detectors that is configured to produce for each point on the object along the image line a respective signal corresponding to the spectrum of a combination of the first and second lines of light after undergoing mutual interference in the analyzer. The signals are processed in known manner to determine the optical properties of the object at each point along the object line. Since the light source is a point light source, the light has high spatial coherence and the interference between the probing beam 220 and the reference beam 240 can be obtained for each point of the illuminated object 350 as long as the light beam 220 returning from the illuminated object is fully covered by the light beam 240 returning from the reference mirror. This OCT can be implemented as a Time Domain—OCT, Swept Source—OCT or Modulated Source—OCT.

In order to obtain Time Domain—OCT, the point light source 100 is a broad band light source. Owing to the cylindrical lens 120, the light illuminates a line on the object 350 and preferably but not necessarily a line on the reference mirror 450. An additional cylindrical lens may be added in orthogonal position relative to the cylindrical lens 150 to focus the reference beam 240 to a spot on the reference mirror 450. The light beams 220 and 240 that return from the object and the reference mirror 450 are combined to a combined beam 260 and focused to a line of light that is directed to a line of detectors constituting the analyzer 550. The intensity on each detector is measured as a function of time while the reference mirror 450 is moved to create continuous different Optical Path Difference (OPDs) between the two light beams 220 and 240. The optical properties of each point of the object at the illuminated line are obtained by analyzing the intensity function at each detector.

Full field Time Domain—OCT can also be implemented using an extended line light source. In this embodiment, the system includes two or more point sources of light 100 arranged along a common line. The first optics 120, 150 is configured to convert each of the point light sources into a respective line light source that is perpendicular to the common line and illuminates a respective line on the object. A beam splitter 200 splits the light exiting the first optics and for each of the point sources directing a respective first portion of the light on to the object 350 as a respective mutually parallel first illuminated line and directing a second portion of the light as a respective mutually parallel second illuminated line on to a reference mirror 450. Second optics 500 collects respective pairs of reflected mutually parallel first lines of light and mutually parallel second lines of light after reflection by the object and mirror of the respective first and second portions of the light and collinearly images the respective reflected first and second lines of light in each pair on to the analyzer 550 as a respective image line to produce for each point on the object along the respective image line a respective signal corresponding to the interference of a combination of the respective first and second lines of light in the respective pair after undergoing mutual interference in the analyzer. In this scheme, the light is spatially coherent in one dimension (perpendicular to the line light source) and is not spatially coherent in the orthogonal dimension (parallel to the line light source).

Full field Time Domain—OCT can also be implemented using the point light source where the object 350 is illuminated with a full-field 2D illumination and its image is imaged on a 2D array of detectors constituting the analyzer 550.

In order to obtain Swept Source—OCT the point light source 100 is a tunable laser and the combined beam 260 is focused on a detectors array. The interferograms are obtained by Fourier transforming the intensity functions of each detector while tuning the wavelengths of the light source. In this case too, a full field 2D object can be measured simultaneously. The object 350 is illuminated by a 2D full field illumination and is imaged on a 2D analyzer having an array of detectors constituting the analyzer 550.

In order to obtain Modulated Source—OCT, the point light source 100 is a spectrally modulated broadband light source. The spectrum of the light source is spectrally modulated with a time varying cosine function by a spectral modulator 110. The combined beam 260 is focused by the optical system 500 onto the analyzer 550 and imaging the object. By modulating the spectrum of the light source with a time varying function, the spectrum of the combined beam 260 can be calculated. For example by modulating the spectrum of the light source with a time varying cosine function, the spectrum of the combined beam 260 can be calculated directly by Fourier transformation of the time intensity function at each detector.

Full field Modulated Source—OCT can also be implemented using an extended line light source. In this embodiment, the first optics 120, 150 is configured to convert each of the point light sources into a respective line light that illuminates a respective line on the object. The line light source is perpendicular to the line that illuminates the respective line on the object. Full field Modulated Source—OCT can also be achieved by illuminating the object 350 with a full field 2D illumination using the point light source, as described above. The extended line light source may include multiple discrete point light sources or may be constituted by a continuous line source wherein, in effect, multiple point light sources are mutually contiguous to form a continuous line source of illumination. In this case also the light is spatially coherent in one dimension (perpendicular to the line light source) and is not spatially coherent in the orthogonal dimension (parallel to the line light source).

The spectral modulator 110 may be any kind of modulator known in the art, such as Michelson interferometer, Fabry Perot interferometer, Spatial Light Modulator etc.

In order to obtain Fourier Domain—OCT, full field Fourier Domain—OCT may be implemented when the light source 100 is a point broadband light source that illuminates the object 350. The light beams 220 and 240 returning from the object 350 and the reference mirror 450 are recombined by the beam splitter 200 to a combined beam 260 that is directed by the imaging system 500 to an imaging spectrometer or a hyperspectral camera constituting the analyzer 550. The spectrum of each point of the line of light is measured simultaneously by the analyzer 550 to obtain the spectrograms of all points at once. The tomography and or the topography of the illuminated object 350 are calculated by analyzing the spectrogram of each point of the combined beam.

The Fourier Domain—OCT can also be implemented in a common path interferometry. In this case the broadband point light source 100 illuminates the object 350. The reflected light propagates through a common path interferometer without the need for a reference mirror and images the object on the imaging spectrometer or hyperspectral camera constituting the analyzer 550.

Another embodiment for implementing the OCT uses Spatial Domain—OCT where the object is scanned one line at a time. The Spatial Domain—OCT is implemented by using a point broadband light source 100 that illuminates the object 350. The light beams 220 and 240 returning from the object 350 and the reference mirror 450 are recombined by the beam splitter 200 to a combined beam 260 that is directed by the imaging system 500 to a line spectrometer constituting the analyzer 550. The spectrum of each point of the line of light is measured simultaneously by the line spectrometer 550 to obtain the spectrograms of all points at once. The tomography and or the topography of the illuminated object 350 are calculated by analyzing the spectrogram of each point of the combined beam.

Figure 2A:
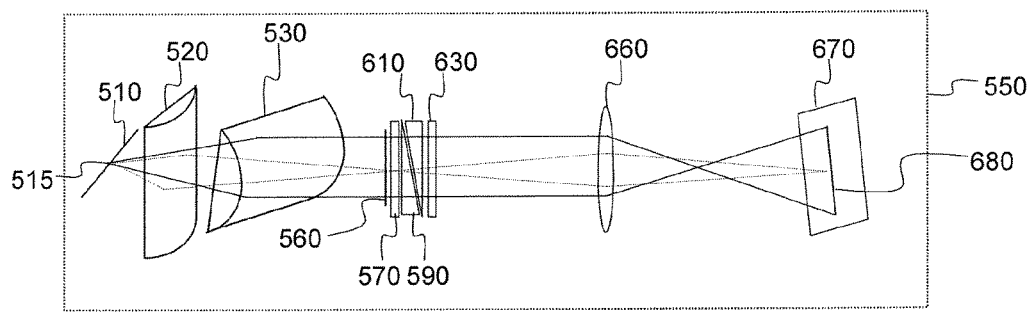
FIG. 2a shows schematically a Spatial Fourier Transform Spectrometer based on birefringence.

The line spectrometer can be based on Spatial Fourier Transform Spectroscopy. One embodiment of a Spatial Fourier Transform Spectrometer (SFTS) is described in FIG. 2a. The SFTS comprises of cylindrical lenses 520 and 530, polarizers 570 and 630, two wedges 590 and 610 made of birefringent materials and a lens 660. In this case, the combined beam 260 (shown in FIG. 1) which its spectrum is to be measured is focused by the imaging system 500 (shown in FIG. 1) to a line of light 510 in the entrance pupil of the line spectrometer constituting the analyzer 550. Each point of the line of light 510 is imaged to a line of light on the polarizer 570 by means of the two orthogonal cylindrical lenses 520 and 530 in such a way that each point of the light line 510 is imaged to a line of light on the polarizer 570 (the solid lines represent the rays in the tangential plane and the dashed lines represent the rays in the sagittal plane). For example, the point 515 is imaged to the line of light 560. The directions of the lines of light on the polarizer 570 are perpendicular to the line of light 510. In one dimension the light is focused and in the other dimension the light is collimated. The polarizer 570, the two thin wedges 590 and 610 and the analyzer 630 are arranged similarly to a fixed Babinet compensator. The polarizer 570 and the analyzer 630 may be mutually parallel or orthogonal. The optical axes of the two wedges 590 and 610 are mutually orthogonal. The direction of the polarizer is preferably 45° to the respective optical axes of the two wedges 590 and 610. The lines of light on the polarizer one of which is 560 are perpendicular to the edge of the wedges 590 and 610. After propagating through the polarizer 570 the line of light 560 is polarized and is preferably oriented 45° relative to both optical axes of the two wedges 590 and 610. The polarized light is divided to two orthogonal polarizations that propagate through the two wedges and acquire a phase difference $\Delta\phi$ whose value is a function of the location on the two wedges. After passing through the two wedges 590 and 610 the light of the line of light 560 propagates through the analyzer 630. The line of light 560 is imaged to a line 680 on a detector array 670 by the lens 660 or imaged directly by proximity imaging on the detector array 670 if it is close to the polarizer 630. The two polarizations interfere on the detectors with constructive or destructive interference according to the phase difference that they acquired. At each point of the line of light 560, the phase difference $\Delta\phi$ between the two orthogonal polarizations depends on the relative thicknesses of the two wedges 590 and 610 at that point. For two symmetrical wedges composed of a positive birefringent material, base width d and prism head angle $\theta$, $\Delta\phi$ is given by:

$$\Delta\phi = \frac{2\pi}{\lambda}(n_e - n_o)[2\tan(\theta)x - d]$$

where $\lambda$ is the wavelength and $n_e$ and $n_o$ are the refractive indices of the extraordinary and the ordinary rays, respectively.

Figure 2B:
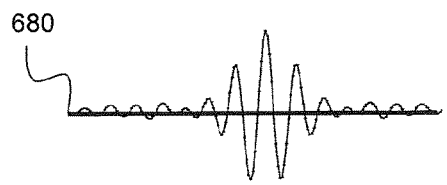

Since the phase difference depends on the wavelength, each component of the light characterized by a different wavelength interferes constructively or destructively according to the respective phase difference between the two polarizations of that component. At each location, each detector integrates the intensities of the interference of all wavelengths to obtain the integrated intensity at that location. The integrated intensity function at each line of detectors represents an interferogram. A typical interferogram which is the intensity function of the line of light 680, is shown in FIG. 2b. The spectrum of the light is obtained by Fourier transforming the interferogram. This applies to all points of light on the line of light 515 each of which is converted to a corresponding line of light by the cylindrical lenses 520 and 530 on the polarizer 570.

It will be appreciated that this approach of spectroscopy can also be implemented for only a single point OCT. The light reflected from a point of the object and the reference mirror is combined and processed by a SFTS as described above.

The system described above can also be placed in the illumination path in order to achieve a spectrally modulated light to obtain a Modulated Source—OCT as described above. In this configuration, each point of the line of light 510 is converted to a line of light where each point of it has a spectrum modulated by varying cosine function. This spectrally modulated light can be used to illuminate an object and scan it as described above.

Figure 3A:
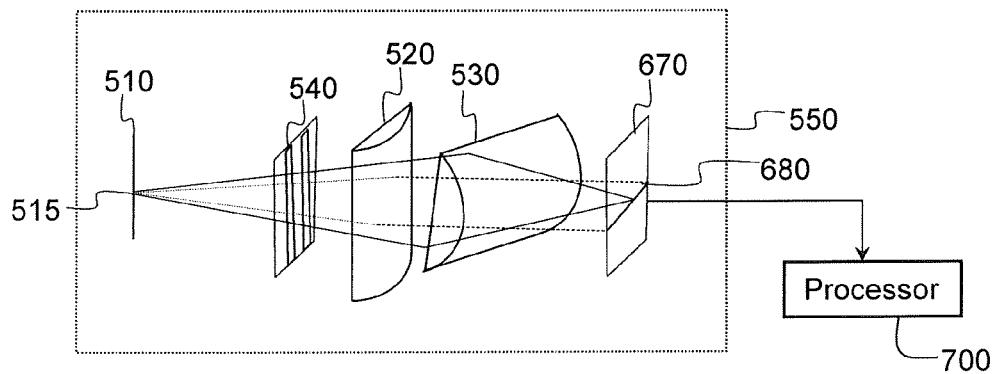
FIG. 3a shows schematically a Spatial Fourier Transform Spectrometer based on interferometry that creates "Equal Inclination fringes" such as Young's slits.
Figure 3B:
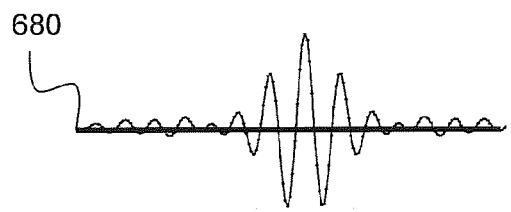
Figure 5:
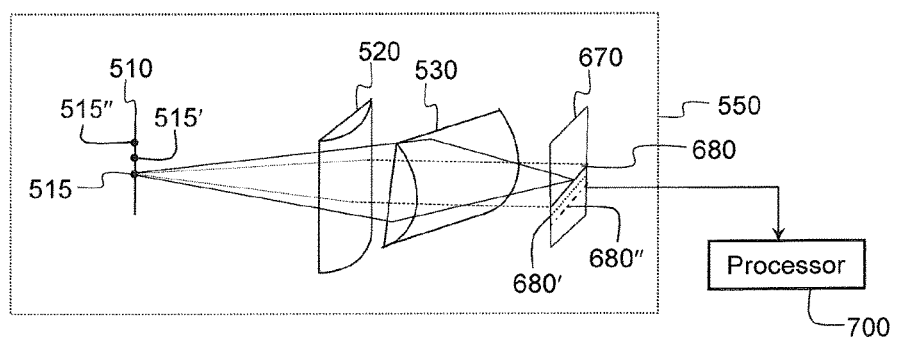
FIG. 5 shows schematically use of cylindrical lenses for area imaging successive points along mutually parallel lines of an object.

In another embodiment, the analyzer 550 is implemented by a line spectrometer as shown in FIG. 3a. In this embodiment, the light beams 220 and 240 that return from the object and the reference mirror 450 are combined to form a combined beam 260 (as shown in FIG. 1) and focused to the line of light 510 on the line spectrometer 550. In the line spectrometer 550, the light from each point of the line of light 510 propagates and its wavefront is separated to two spatial parts such as in Young's slits experiment, and the two parts of the wavefront are forced to interfere and create a fringe pattern. These fringes are called "Equal Inclination fringes" since at each point the rays that interfere have equal inclination. For example, the light from each point of the line of light 510 such as point 515 propagates and is diffracted by the two slits 540. The slits 540 constitute third optics for splitting respective wavefronts emanating from each point of light along the image line into respective spatially separated components. Behind the two slits, the two cylindrical lenses 520 and 530 create two different focal lengths for the two mutually orthogonal spatial dimensions, being respectively parallel and orthogonal to the image line, and such that in the dimension parallel to the slits the detector array 670 is located at the image plane of the line of light 510 but in the direction perpendicular to the slits the detector array is located at a focal plane of the optical system. Thus, the rays of light from each point of the line of light 510 are focused in one dimension and are collimated in the other dimension. In other words, the separated components of each wavefront mutually interfere on the focal plane to produce equal inclination fringes. This configuration creates a line of light 680 on a different line of detectors in the detector array 670 for each point of the line of light 510. Each line of light such as the line of light 680 is the interference pattern of the two slits for a single light point such as 515. The imaging of multiple lines is best seen in FIG. 5 where successive points 515, 515' and 515" on the line 510 are imaged as respective parallel lines 680, 680' and 680" on the detector array 670. Each wavelength has its diffraction pattern which has spatial dimensions that depend on the wavelength. Each detector integrates the intensities of the diffraction patterns of all wavelengths and produces respective signals that are processed by a processor 700 to determine the optical properties of the object at each point along the object line. The processor 700 may be part of the line spectrometer constituting the analyzer 550 or may be external thereto as shown in FIGS. 3 and 5. The integrated intensity function at each line of detectors perpendicular to the two slits represents an interferogram. A typical interferogram which is the intensity function of the line of light 680, is shown in FIG. 3b. The spectrum of the light of each point such as 515 is obtained by Fourier transforming the interferogram. The distance between the two slits can be varied to increase or decrease the spatial resolution of detection of the intensity function and thus the spectral resolution.

This approach can also be implemented in other embodiments such as using Fresnel's biprism or Lloyd's mirrors or any other optical device that creates "Equal Inclination Fringes". In all embodiments the light from each point of the line of light 510 is focused in one dimension and creates an interference pattern in the other dimension on a line of detectors on the detectors array which is perpendicular to the two slits, as described above.

This approach can also be implemented in a single point OCT. In one embodiment, the combined beam 260 (for a single point) is focused and coupled to an optical fiber. The light is split to two optical fibers by means of a 3 dB coupler or some other means. The light outgoing from the two fibers interfere and creates an interference pattern of two pinholes on a line array of detectors. The spectrum of the light is obtained by Fourier transforming the interferogram which is actually the interference pattern obtained on the detector array. The distance between the two fibers tips can be varied to increase or decrease the spatial resolution of detection of the intensity function and thus the spectral resolution.

In all cases described above the envelope function of the diffraction that modulates the interference pattern can be compensated by proper algorithms.

Figure 4A:
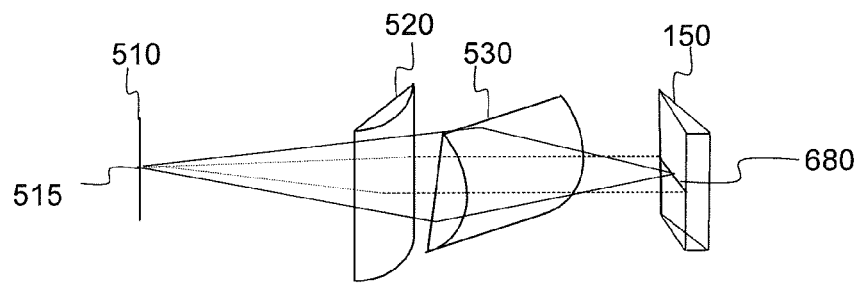
FIG. 4a shows schematically a Spatial Fourier Transform Spectrometer based on interferometry that creates "Equal thickness fringes" such as a wedge.
Figure 4B:
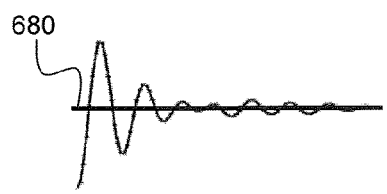

In another embodiment according to the present invention, the analyzer 550 is a line spectrometer implemented using Spatial Domain—OCT by means of optical elements or systems that create "Equal Thickness fringes" such as a wedge 150 as shown in FIG. 4a. In this embodiment, the line light beams 220 and 240 that return from the object and the reference mirror 450 are combined to form the combined beam 260 (shown in FIG. 1) and focused to the line of light 510 on the line spectrometer, as described above. In the line spectrometer, the light of the line of light 510 propagates through the cylindrical lenses 520 and 530 and illuminates the wedge 150. The cylindrical lenses 520 and 530 are configured such that in the dimension parallel to line of light 510 the wedge 150 is located at the image plane of the line of light 510 and the rays of light from each point of the line of light 510 are focused, but in the dimension perpendicular to the light of the line of light 510 the rays of light from each point along the line of light 510 are collimated. In such case, each point of the line of light 510 is imaged to a line 680 on the wedge 150 by the cylindrical lens 520 and 530. In the wedge 150, part of the light is reflected from the upper side of the wedge and part of the light is reflected from the lower side of the wedge. The two reflected parts of light interfere and the interference creates a fringe pattern according to the phase delay between the two parts of light. These fringes are called "Equal Thickness Fringes" since the phase delay depends on the wedge's thickness at a certain location. Since the phase difference depends also on the wavelength, each wavelength interferes in a constructive or a destructive interference according to its phase difference and creates its own fringe pattern. The fringe patterns are imaged on a detector array in reflective or transmissive mode. At each location, each detector integrates the intensities of the interference of all wavelengths to obtain the integrated intensity at that location. The integrated intensity function at each line of detectors represents an interferogram. A typical interferogram which is the intensity function of the line of light 680, is shown in FIG. 4b. The spectrum of the light is obtained by Fourier transforming the interferogram.

This approach can also be implemented in any other optical systems such as Fizeau interferometer that create "Equal Inclination Fringes".

This approach can also be implemented in a single point OCT where the wedge can also be replaced by an axicon.

It is also understood that all embodiments described above can also serve as spectrometers not only for OCT but also for other applications, especially in the medical imaging regime, and may include for example different endoscopic devices and hyper spectral imaging systems.

It will also be understood that while the line spectrometers described with reference to FIGS. 3a and 4a are a component in a system for analyzing optical properties of an object, the line spectrometers can be used in many other applications. As such, the line spectrometers are amenable to independent use and the invention encompasses the line spectrometers per se.

It should be noted that features that are described with reference to one or more embodiments are described by way of example rather than by way of limitation to those embodiments. Thus, unless stated otherwise or unless particular combinations are clearly inadmissible, optional features that are described with reference to only some embodiments are assumed to be likewise applicable to all other embodiments also.

The invention claimed is:

1. Apparatus comprising:
a line spectrometer configured to receive at least one point of light, the line spectrometer comprising:
a first optical element; and
a second optical element configured to convert the point of light to a line of light and to direct the line of light toward the first optical element,
the first optical element defining first and second surfaces, a distance between the first and second surface varying as a function of distance along the first optical element in a direction that is perpendicular to the line of light, the first optical element thereby being configured to generate first and second reflected lines of light that reflect respectively from the first and second surfaces of the first optical element,
a detector array configured to receive the first and second lines of light, and to generate an interferogram in response thereto; and
a computer processor configured to determine a spectrum of the point of light, by analyzing the interferogram.

2. The apparatus according to claim 1, wherein the first optical element comprises a wedge.

3. The apparatus according to claim 1, wherein the first optical element comprises an axicon.

4. The apparatus according to claim 1, wherein the second optical element comprises a cylindrical lens.

5. The apparatus according to claim 1, wherein the line spectrometer is configured to receive two or more points of light arranged along a common line of light.

6. The apparatus according to claim 1, wherein the apparatus is for use with an object, and wherein the line spectrometer is configured to receive the at least one point of light by receiving at least one point of light that reflected from object.

7. The apparatus according to claim 6, wherein the computer processor is configured to determine an optical property of the object by analyzing the interferogram.

8. The apparatus according to claim 1,
wherein the apparatus is for use with an object,
the apparatus further comprising:
at least one point source of light that is configured to generate light that contains a plurality of spectral bands, each spectral band having a respective amplitude, phase and polarization;
first optics configured to convert light from the point light source into a line of light;
a reference mirror;
a beam splitter configured to split the line of light, such as to direct a first portion of the line of light on to the object and illuminate an object line on the object, and such as to direct a second portion of the line of light on to the reference mirror;
second optics configured to collect reflected first and second lines of light after reflection by the object and mirror of, respectively, the first and second portions of the line of light, and configured to collinearly image the reflected first and second lines of light as an image line on to the line spectrometer, wherein:
the second optical element is configured to convert each respective point on the image line to respective image-line-derived lines of light that are perpendicular to the image line and to direct each of the image-line-derived lines of light toward the first optical element, such that first and second reflected image-line-derived lines of light reflect respectively from the first and second surfaces of the first optical element,
the detector array is configured to receive the first and second reflected image-line-derived lines of light for each of the points on the image line, and to generate respective interferograms in response thereto, each interferogram corresponding to a respective point along the object line, and
the computer processor is configured to determine the optical properties of the object at each point along the object line, based upon the interferograms.

9. The apparatus according to claim 8, wherein the reference mirror is moveable.

10. The apparatus according to claim 8, wherein the first optics comprises at least one cylindrical lens.

11. The apparatus according to claim 8, wherein the second optics comprises at least one cylindrical lens.

12. The apparatus according to claim 8, wherein the point source of light comprises a spectrally modulatable point source of light.

13. The system according to claim 8, wherein:
the at least one point source of light comprises two or more point sources of light arranged along a common line;
the first optics are configured to convert light from each of the point light sources into a respective line of light;
the beam splitter is configured to split the lines of light corresponding to each of the point sources, such as to direct a respective first portion of the line of light on to the object as a respective mutually parallel object line that illuminates the object, and to direct a second portion of the line of light as a respective mutually parallel second illuminated line on to the reference mirror;
the second optics are configured to collect respective pairs of reflected mutually parallel first lines of light and mutually parallel second lines of light after reflection by the object and mirror of the respective first and second portions of the lines of light and are configured to collinearly image the respective reflected first and second lines of light in each pair on to the line spectrometer as a respective image line;
the detector array is configured to generate, for each point on the object, a respective set of interferograms corresponding to combination of the respective sets of first and second image-line-derived lines of light after reflecting from the first and second surfaces of first optical element in the line spectrometer; and
the computer processor is configured to determine the optical properties of the object at each point along each of the plurality of object lines, based upon the sets of interferograms.

14. The apparatus according to claim 13, wherein the two or more point sources of light comprise a line illumination source.

15. The apparatus according to claim 13, wherein each of the point sources of light comprises a spectrally modulatable point source of light.

16. A method comprising:
using a line spectrometer that includes an optical element:
receiving at least one point of light:
converting the point of light to a line of light, and directing the line of light toward the optical element, the optical element defining first and second surfaces, a distance between the first and second surface varying as a function of distance along the optical element in a direction that is perpendicular to the line of light, such that by directing the line of light toward the optical element, first and second reflected lines of light are generated that reflect respectively from the first and second surfaces of the optical element, using a detector array:
receiving the first and second lines of light; and
generating an interferogram in response thereto; and using a computer processor, determining a spectrum of the point of light, by analyzing the interferogram.

17. The method according to claim 16, wherein the optical element includes a wedge, and directing the line of light toward the optical element comprises directing the line of light toward the wedge.

18. The method according to claim 16, wherein the optical element includes an axicon, and directing the line of light toward the optical element comprises directing the line of light toward the axicon.

19. The method according to claim 16,
further comprising:
generating at least one point of light that contains a plurality of spectral bands, each spectral band having a respective amplitude, phase and polarization;
converting the point of light into a line of light;
splitting the line of light, such as to direct a first portion of the line of light on to an object such as to illuminate an object line on the object, and such as to direct a second portion of the line of light on to a reference mirror;
collecting reflected first and second lines of light after reflection by the object and mirror of, respectively, the first and second portions of the line of light; and
collinearly imaging the reflected first and second lines of light as an image line on to the line spectrometer,
wherein:
converting the point of light to the line of light comprises converting each respective point on the image line to respective image-line-derived lines of light that are perpendicular to the image line;
directing the line of light toward the optical element comprises directing each of the image-line-derived lines of light toward the optical element, such that first and second reflected image-line-derived lines of light reflect respectively from the first and second surfaces of the optical element,
receiving the first and second lines of light comprises receiving the first and second reflected image-line-derived lines of light for each of the points on the image line;

generating the interferogram comprises generating respective interferograms, each interferogram corresponding to a respective point along the object line, and determining the spectrum of the point of light by analyzing the interferogram comprises determining optical properties of the object at each point along the object line based upon the interferograms.

20. The method according to claim 19, further comprising modulating a spectrum of the generated light.

21. The system according to claim 19, wherein:
generating the at least one point of light comprises generating a plurality of points of light;
converting the point of light into the line of light comprises converting each of the points of light into a respective line of light;
splitting the line of light comprises splitting the lines of light and for each of the lines of light directing a respective first portion of the line of light on to the object as a respective mutually parallel object line that illuminates the object, and for each of the lines of light directing a second portion of the line of light as a respective mutually parallel second illuminated line on to the reference mirror;
collecting reflected first and second lines of light comprises collecting respective pairs of reflected mutually parallel first lines of light and mutually parallel second lines of light after reflection by the object and mirror of the respective first and second portions of the lines of light;
collinearly imaging the reflected first and second lines of light as the image line on to the line spectrometer comprises collinearly imaging the respective reflected first and second lines of light in each pair on to the line spectrometer as a respective image line;
generating the interferogram comprises generating, for each point on the object, a respective set of interferograms corresponding to combination of the respective sets of first and second image-line-derived lines of light after reflecting from the first and second surfaces of optical element in the line spectrometer; and
determining optical properties of the object at each point along the object line comprises determining optical properties of the object at each point along each of the plurality of object lines, based upon the sets of interferograms.

22. The method according to claim 19, generating the plurality of points of light comprises generating a line of light.

* * * * *